(12) United States Patent
Lecuivre et al.

(10) Patent No.: US 11,826,242 B2
(45) Date of Patent: Nov. 28, 2023

(54) SYNTHETIC PROSTHESIS COMPRISING A KNIT AND A NON POROUS FILM AND METHOD FOR FORMING SAME

(71) Applicants: Sofradim Production, Trévoux (FR); Covidien LP, Mansfield, MA (US)

(72) Inventors: Julie Lecuivre, Rhone (FR); Nicolas Prost, Rhone (FR); Nicholas Maiorino, Branford, CT (US); Matthew Prescott, North Haven, CT (US); Thomas Corso, West Haven, CT (US)

(*) Notice: Subject to any disclaimer, the term of this patent is extended or adjusted under 35 U.S.C. 154(b) by 697 days.

(21) Appl. No.: 16/839,095

(22) Filed: Apr. 3, 2020

(65) Prior Publication Data

US 2020/0246124 A1 Aug. 6, 2020

Related U.S. Application Data

(62) Division of application No. 15/169,829, filed on Jun. 1, 2016, now Pat. No. 10,743,976.

(30) Foreign Application Priority Data

Jun. 19, 2015 (EP) .................................... 15305947

(51) Int. Cl.
*A61F 2/00* (2006.01)
*A61L 27/58* (2006.01)
(Continued)

(52) U.S. Cl.
CPC ............ *A61F 2/0063* (2013.01); *A61L 27/16* (2013.01); *A61L 27/18* (2013.01); *A61L 27/58* (2013.01);
(Continued)

(58) Field of Classification Search
CPC .... A61F 2/0063; A61F 2/0077; A61F 2/0045; A61F 2210/0004; A61F 2250/0097;
(Continued)

(56) References Cited

U.S. PATENT DOCUMENTS 1,187,158 A 6/1916 Mcginley
3,054,406 A 9/1962 Usher
(Continued)

FOREIGN PATENT DOCUMENTS

CA 1317836 C 5/1993
CN 201879864 U 6/2011
(Continued)

OTHER PUBLICATIONS

Notification of the First Office Action issued in Chinese Patent Application No. 201610439577.1 dated May 20, 2020, 19 pages; with Eng. translation.

(Continued)

*Primary Examiner* — Mohamed G Gabr
(74) *Attorney, Agent, or Firm* — WEBER ROSSELLI & CANNON LLP (57) ABSTRACT

The present invention relates to a synthetic prosthesis for tissue reinforcement comprising:
  a porous knit made from a monofilament of a synthetic biocompatible material, said knit defining two opposite faces, a first face and a second face,
  a synthetic non porous biodegradable film comprising at least a copolymer of at least ε-caprolactone, said film covering at least part of said first face,
  a synthetic biodegradable binder bonding said film to said first face, said binder comprising at least a polymer of ε-caprolactone,
  wherein said second face of said porous knit is left open to cell colonization.

(Continued)

The invention also relates to a method for forming such a prosthesis.

15 Claims, 1 Drawing Sheet

(51) Int. Cl.
- *A61L 31/14* (2006.01)
- *A61L 31/06* (2006.01)
- *A61L 27/16* (2006.01)
- *A61L 27/18* (2006.01)

(52) U.S. Cl.
CPC ............. *A61L 31/06* (2013.01); *A61L 31/146* (2013.01); *A61F 2002/009* (2013.01); *A61F 2002/0068* (2013.01); *A61F 2210/0004* (2013.01); *A61F 2240/00* (2013.01); *A61F 2250/0097* (2013.01)

(58) Field of Classification Search
CPC ...... A61F 2250/0026; A61F 2250/0031; A61F 2250/0062; A61F 2250/0085; A61F 2250/0098; A61F 2002/0068; A61F 2002/009; A61F 2002/30322; A61F 2220/0016; A61F 2240/00
See application file for complete search history.

(56) References Cited

U.S. PATENT DOCUMENTS

| | | |
|---|---|---|
| 3,118,294 A | 1/1964 | Van Laethem |
| 3,124,136 A | 3/1964 | Usher |
| 3,272,204 A | 9/1966 | Artandi et al. |
| 3,276,448 A | 10/1966 | Kronenthal |
| 3,320,649 A | 5/1967 | Naimer |
| 3,364,200 A | 1/1968 | Ashton et al. |
| 3,570,482 A | 3/1971 | Shigeru et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Melton et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | Mcmurray |
| 5,350,583 A | 9/1994 | Yoshizato et al. |
| 5,356,432 A | 10/1994 | Rutkow et al. |
| 5,368,549 A | 11/1994 | Mcvicker |
| 5,368,602 A | 11/1994 | Torre |
| 5,370,650 A | 12/1994 | Jonathan et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,090 A | 11/1997 | Schilder et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |

(56) References Cited

U.S. PATENT DOCUMENTS

| | | |
|---|---|---|
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | Mcgregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Robert |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D Aversa et al. |
| 6,113,623 A | 9/2000 | Sgro |
| 6,120,539 A | 9/2000 | Eldridge et al. |
| 6,132,765 A | 10/2000 | Dicosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | Macphee et al. |
| 6,197,934 B1 | 3/2001 | Devore et al. |
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Robert |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | Devore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Mueller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Bryan et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |

(56) References Cited

U.S. PATENT DOCUMENTS

| | | |
|---|---|---|
| 6,736,854 B2 | 5/2004 | Vadurro et al. |
| 6,737,371 B1 | 5/2004 | Planck et al. |
| 6,743,435 B2 | 6/2004 | Devore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III et al. |
| 7,682,381 B2 | 3/2010 | Rakos et al. |
| 7,709,017 B2 | 5/2010 | Tayot et al. |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2002/0087174 A1 | 7/2002 | Capello |
| 2002/0095218 A1 | 7/2002 | Carr et al. |
| 2003/0086975 A1 | 5/2003 | Ringeisen |
| 2003/0106346 A1 | 6/2003 | Matsumoto |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | Mcalexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0105526 A1 | 4/2009 | Piroli et al. |

(56) References Cited

U.S. PATENT DOCUMENTS

| | | |
|---|---|---|
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li et al. |
| 2009/0318752 A1 | 12/2009 | Evans et al. |
| 2010/0104608 A1 | 4/2010 | Abuzaina et al. |
| 2010/0318108 A1* | 12/2010 | Datta ................... A61L 31/146 606/151 |
| 2011/0015760 A1 | 1/2011 | Kullas |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet et al. |
| 2011/0257666 A1 | 10/2011 | Ladet et al. |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell et al. |
| 2012/0179176 A1 | 7/2012 | Wilson et al. |
| 2012/0197415 A1 | 8/2012 | Montanari et al. |
| 2014/0005341 A1* | 1/2014 | Tang ................... C08G 63/08 525/411 |
| 2014/0044861 A1 | 2/2014 | Boey et al. |
| 2014/0364684 A1 | 12/2014 | Lecuivre et al. |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 0544485 A1 | 6/1993 |
| EP | 0552576 A1 | 7/1993 |
| EP | 0611561 A1 | 8/1994 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 0827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 0898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1216717 A1 | 6/2002 |
| EP | 1216718 A1 | 6/2002 |
| EP | 0693523 B1 | 11/2002 |
| EP | 1273312 A2 | 1/2003 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| EP | 2792351 A1 | 10/2014 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2724563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 B1 | 12/2005 |
| FR | 2876020 A1 | 4/2006 |
| FR | 2863277 B1 | 6/2006 |
| FR | 2884706 B1 | 4/2008 |
| FR | 2929834 A1 | 10/2009 |
| FR | 2953709 A1 | 6/2011 |
| GB | 1174814 A | 12/1969 |
| GB | 2051153 A | 1/1981 |
| GB | 2306110 A | 4/1997 |
| JP | H0332677 U | 3/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| JP | 2013535244 A | 9/2013 |
| JP | 2014514037 A | 6/2014 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9310731 A1 | 6/1993 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |
| WO | 9641588 A1 | 12/1996 |
| WO | 9735533 A1 | 10/1997 |
| WO | 9835632 A1 | 8/1998 |
| WO | 9849967 A1 | 11/1998 |
| WO | 9905990 A1 | 2/1999 |
| WO | 9906079 A1 | 2/1999 |
| WO | 9906080 A1 | 2/1999 |
| WO | 9951163 A1 | 10/1999 |
| WO | 0016821 A1 | 3/2000 |
| WO | 0067663 A1 | 11/2000 |
| WO | 0115625 A1 | 3/2001 |
| WO | 0180773 A1 | 11/2001 |
| WO | 0181667 A1 | 11/2001 |
| WO | 0207648 A1 | 1/2002 |
| WO | 0217853 A2 | 3/2002 |
| WO | 02078568 A1 | 10/2002 |
| WO | 03002168 A1 | 1/2003 |
| WO | 2004004600 A1 | 1/2004 |
| WO | 2004071349 A2 | 8/2004 |
| WO | 2004078120 A2 | 9/2004 |

(56) References Cited

FOREIGN PATENT DOCUMENTS

| | | |
|---|---|---|
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023444 A2 | 3/2006 |
| WO | 2006032812 A2 | 3/2006 |
| WO | 2009071998 A2 | 6/2009 |
| WO | 2009031035 A3 | 1/2010 |
| WO | 2010043978 A2 | 4/2010 |
| WO | 2010088699 A2 | 8/2010 |
| WO | 2007048099 A3 | 9/2010 |
| WO | 2011007062 A1 | 1/2011 |
| WO | 2011026987 A1 | 3/2011 |
| WO | 2011038740 A1 | 4/2011 |
| WO | 2012007578 A1 | 1/2012 |
| WO | 2012123582 A1 | 9/2012 |

OTHER PUBLICATIONS

Amid, P., "Lichtenstein tension-free hernioplasty Its inception, evolution, and principles," Hernia, 2004; pp. 1-7, 8, published online Sep. 2003.
Blondin, C. et al., "Inhibition of Complement Activation by Natural Sulfated Polysaccharides (*Fucans*) from Brown Seaweed," Molecular Immuol., Mar. 1994, pp. 247-253, 31(4).
Blondin, C. et al., "Relationships between chemical characteristics and anticomplementary activity of fucans," Biomaterials, Mar. 1996, pp. 597-603, 17(6).
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Chen, G. et al., "A Hybrid Network of Synthetic Polymer Mesh and Collagen Sponge," The Royal Society of Chemistry 2000, Chem. Commun., Jul. 2000, pp. 1505-1506.
Collins, R. et al., "Use of collagen film as a dural substitute: Preliminary animal studies," Journal of Biomedical Materials Research, Feb. 1991, pp. 267-276, vol. 25.
Dr. S. Raz, "The Karl Mayer Guide to Tehnical Textiles," Jan. 2000, pp. 1-36, Obertshausen, Germany.
European Search Report for EP 15 30 5947 date of completion is Nov. 25, 2015 (4 pages).
Examination report No. 1 for standard patent application issued in Australian Patent Application No. 2016203147 dated Feb. 13, 2020, 4 pages.
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Haroun-Bouhedja, F. et al., "Relationship between sulfate groups and biological activities of fucans," Thrombosis Res., Dec. 2000, pp. 453-459, 100(5).

Hirano, S. et al., "The blood biocompatibility of chitosan and N-acylchitosans," J. Biomed. Mater. Res., Apr. 1985, 413-417, 19.
Junge, K. et al., "Functional and Morphologic Properties of a Modified Mesh for Inguinal Hernia Repair," World J. Surg., Sep. 2002, pp. 1472-1480, 26.
Kanabar, V. et al., "Some structural determinants of the antiproliferative effect of heparin-like molecules on human airway smooth muscle," Br. J. Pharmacol., Oct. 2005, pp. 370-777, 146(3).
Klinge, U. et al., "Foreign Body Reaction to Meshes Used for the Repair of Abdominal Wall Hernias," Eur J. Surg, Sep. 1999, pp. 665-673, 165.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Langenbech, M. R. et al., "Comparison of biomaterials in the early postoperative period," Surg Endosc., May 2003, pp. 1105-1109, 17 (7).
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Malette, W. G. et al., "Chitosan, a New Hemostatic," Ann Th. Surg., Jul. 1983, pp. 55-58, 36.
Mühl, T. et al., "New Objective Measurement to Characterize the Porosity of Textile Implants," Journal of Biomedical Materials Research Part B: Applied Biomaterials, May 2007, pp. 176-183.
Muzzarelli, R. et al., "Reconstruction of parodontal tissue with chitosan," Biomaterials, Nov. 1989, pp. 598-604, 10.
Notice of Reasons for Rejection issued in Japanese Patent Application No. 2016-108408 dated Feb. 17, 2020, with English translations, 8 pages.
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Prokop, A. et al., "Water Soluble Polymers for Immunoisolation I: Complex Coacevation and Cytotoxicity," Advances in Polymer Science, Jul. 1998, pp. 1-51, 136.
Rao, B. et al., "Use of chitosan as a biomaterial: Studies on its safety and hemostatic potential," J. Biomed. Mater. Res., Jan. 1997, pp. 21-28, 34.
Rosen, M. et al., "Laparoscopic component separation in the single-stage treatment of infected abdominal wall prosthetic removal," Hernia, 2007, pp. 435-440, 11, published online Jul. 2007.
Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).
Strand, S. et al., "Screening of Chitosans and Conditions for Bacterial Flocculation," Biomacromolecules, Mar. 2001, 126-133, 2.
Varum, K. et al., "In vitro degradation rates of partially N-acetylated chitosans in human serum," Carbohydrate Research, Mar. 1997, pp. 99-101, 299.
Welty, G. et al., "Functional impairment and complaints following incisional hernia repair with different polypropylene meshes," Hernia, Aug. 2001; pp. 142-147, 5.
Zvyagintseva,, T. et al., "Inhibition of complement activation by water-soluble polysaccharides of some far-eastern brown seaweeds," Comparative Biochem and Physiol, Jul. 2000, pp. 209-215,126(3).
Decision of Rejection issued in Chinese Application No. 201610439577.1 dated Jan. 28, 2021, with English Translation.

* cited by examiner

SYNTHETIC PROSTHESIS COMPRISING A KNIT AND A NON POROUS FILM AND METHOD FOR FORMING SAME

CROSS-REFERENCE TO RELATED APPLICATIONS

This application is a divisional of U.S. patent application Ser. No. 15/169,829 filed Jun. 1, 2016, which claims the benefit of and priority to European Patent Application Serial No. 15305947.2 filed Jun. 19, 2015, and the disclosures of each of the above-identified applications are hereby incorporated by reference in their entirety.

TECHNICAL FIELD

The present invention relates to a synthetic prosthesis for tissue reinforcement, the prosthesis comprising a porous knit and a biodegradable adhesion barrier film provided on one face of said knit. The prosthesis of the invention is particularly intended for the reinforcement of soft tissue where a weakness exists such as the primary abdominal wall and incisional hernias.

BACKGROUND OF RELATED ART

Reinforcement prostheses, for example prostheses for reinforcing the abdominal wall, are widely used in the surgical field. These prostheses are intended to treat hernias by temporarily or permanently filling a tissue defect. These prostheses are generally made of biocompatible prosthetic fabric, for example knits, and can have a number of shapes, for example rectangular, circular or oval, depending on the anatomical structure to which they are to be fitted.

Prosthetic fabrics such as knits are intrinsically adhesiogenic and fibrogenic, irrespective of the nature of the tissues with which they are put in contact. It is desirable to provide reinforcement prostheses that, although based on prosthetic fabric, also prevent post-surgical adhesions, especially when they are positioned intraperitoneally.

Postsurgical adhesions include all non-anatomical fibrous connections accidentally induced by a surgical act during the normal process of cicatrization. They may occur in all surgical disciplines regardless of the operation in question. Postsurgical adhesions can provoke syndromes which can be classed principally as chronic pain, occlusive syndromes and female infertility. Furthermore, they increase very substantially the risks of making errors in follow-up surgery, while prolonging the operating times, since the preliminary dissection can be very awkward in such cases.

To remedy this problem, it was suggested to render one face of these reinforcement prostheses completely smooth during the initial inflammatory phase, and therefore not favorable to the generation of adhesions. To do this, a physical barrier is interposed between the structures which are not intended to adhere to each other.

However, the desired barrier effect poses the problem of the intrinsic adhesive power of this barrier. The reason is that if the barrier is made of a non biodegradable material, it can itself be the source of adhesions over the course of time; and if it is biodegradable, its biodegradation must be sufficiently noninflammatory so as not to cause adhesions itself on one hand, and on the other hand, its biodegradation kinetics should be appropriate so as to allow the barrier to remain integrate during the time needed for it to perform its function of prevention of formation of adhesions.

SUMMARY

In the present application, the term "biodegradable" is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

In the present application, the term "non biodegradable" is defined to include both non bioabsorbable and non bioresorbable materials. By non biodegradable, it is meant that the materials do not decompose under body conditions and remain permanently in the body.

Adhesion barrier films are known, that are obtained via gelling of a starting solution comprising collagen. The collagen may be derived from animal or human sources. Anyway, prosthesis involving animal human derived biological materials are not always reproducible or compatible.

Moreover, it was found that the films of the prior art used as a barrier for the prevention of post-surgical adhesions may lack mechanical strength and resistance, and may delaminate once implanted. The film therefore separates from the prosthetic fabric within the body of the patient and can not perform its adhesion barrier function.

There is therefore a need for a prosthesis that would be entirely synthetic and that would comprise a fully biodegradable adhesion barrier film, said film being nevertheless resistant to delamination at least for the time necessary for it to prevent occurrence of adhesions, namely for at least 1 to 2 weeks.

In addition, in order to minimize the trauma subsequent to any surgical intervention, patients are increasingly operated by laparoscopy when the type of intervention performed allows this. Laparoscopy requires only very small incisions through which a trocar is passed, with the prosthesis being conveyed inside the trocar to the implantation site. Open surgery is thus avoided, and the patient can soon leave hospital. Laparoscopy is particularly popular in surgical interventions performed in the abdomen, for example the treatment of hernias.

However, the trocars used in laparoscopic surgery generally have a relatively small calibrated diameter, which may vary, for example, from 5 to 15 mm, in order to reduce as much as possible the size of the incision that is made. The prosthesis therefore has to be conveyed to the implantation site within a conduit of small diameter. The prosthesis is generally rolled up on itself in order to make it slide in the conduit of the trocar or is introduced directly by force, if appropriate with the aid of laparoscopy forceps.

There is therefore still the need for a prosthesis based on a knit provided with a biodegradable adhesion barrier film on one of its faces, that is soft enough to be pliable and to be foldable so that it can be easily introduced into a conduit such as that of a trocar of small diameter, without damaging the knit and the film.

Moreover, reinforcement prostheses are all the more effective and their local tolerance is all the better, the earlier and the more intimate their tissue integration. For this reason, the most effective of the known prosthetic fabrics for these indications are generally porous and are designed in such a way as to be integrated in the body as rapidly as possible.

In the present application, the term "porous" is intended to signify the characteristic according to which the faces and the thickness of the textile it refers to, such as a fabric or a knit, present pores, voids, alveoli, distributed regularly or irregularly, and promoting all cell colonization, on the surface and within/through the thickness of the textile.

In the present application, the term «non-porous» is intended to signify that the structure it refers to, such as a film, presents a smooth and even surface devoid of any pores, such a surface preventing the occurrence of postsurgical adhesions.

Moreover, in a view of reducing the foreign material implanted into the body of a patient, it is desired to produce lightweight reinforcement prostheses. In addition, for facilitating the work of the surgeon at the time he puts the prosthesis in place at the implantation site, it is further desired that the prosthesis show a good transparency. Lightweight knits showing a plurality of pores, and preferably large pores, are therefore desirable for forming lightweight reinforcement prostheses favoring a good tissue ingrowth.

There is therefore a need for a synthetic prosthesis that could be used for tissue reinforcement, for example for the reinforcement of soft tissue where a weakness exists such as the primary abdominal wall and incisional hernias, in an intraperitoneal position, possibly by laparoscopy, that would offer cell recolonization and tissue integration properties on one of its faces, while being provided on its other face with a biodegradable adhesion barrier film preventing or at least minimizing postsurgical adhesions, at least during the 4 weeks following surgery, said film being not subject to delamination. The synthetic prosthesis should also preferably minimize the amount of foreign material implanted in the body of the patient.

A first aspect of the invention is a synthetic prosthesis for tissue reinforcement comprising:

a porous knit made from a monofilament of synthetic biocompatible material, said knit defining two opposite faces, a first face and a second face, a synthetic non porous biodegradable film comprising at least a copolymer of at least ε-caprolactone, said film covering at least part of said first face, a synthetic biodegradable binder bonding said film to said first face, said binder comprising at least a polymer of ε-caprolactone, wherein said binder is present between said film and said first face under the form of a discontinuous layer, and wherein said second face of said porous knit is left open to cell colonization.

The prosthesis of the invention comprises two faces which are different in their respective appearances and functions, namely one face which is porous or open on one side, in order to accommodate and direct the postsurgical cell colonization, and the other face which is closed, for tissue separation without adhesion at least during the time post-surgical adhesions are likely to occur.

The prosthesis of the invention allows therefore cell colonization and tissue integration to take place on one hand, via the second face of the porous knit, while minimizing the development of adhesions on its opposite face, namely the first face of the knit which is covered by the non porous biodegradable film acting as an adhesion barrier film for at least 1 to 2 weeks.

The film is intimately linked to the first face of the knit by the binder, and cannot be delaminated, while at the same time maintaining the porosity open on the second surface of the knit.

Moreover, the cooperation of the knit, the film and the binder of the prosthesis of the invention makes it possible for tissue colonization to develop immediately, independently of complete degradation of the biodegradable film, which itself is relatively rapid, for example occurring in about 4 to 15 weeks without compromising the performance of the prosthesis. In addition, the structure of the binder, which is present under the form of a discontinuous layer of material, allows the cell colonization and tissue integration to further develop on the first face of the porous knit when the non porous film begins biodegrade after a few weeks, at a time when post-surgical adhesions are no more likely to occur and the non porous film has completed its function of prevention of adhesions.

The prosthesis of the invention is formed of synthetic materials only. Synthetic materials have the advantage of being reproducible and their behavior is well known.

In addition, the presence of a common chemical component, such as ε-polycaprolactone, both in the non porous film and in the binder of the prosthesis of the invention allows reducing the number of foreign materials of different compositions that are implanted in the body of the patient.

The prosthesis of the invention is particularly adapted to the reinforcement of abdominal wall soft tissue where a weakness exists in procedures involving primary and incisional abdominal wall hernia surgeries.

The prosthesis of the invention comprises a porous knit made from a monofilament of a synthetic biocompatible material, said knit defining two opposite faces, a first face and a second face.

The knit of the invention is made from a monofilament of a synthetic biocompatible material.

The synthetic biocompatible material may be biodegradable, non-biodegradable or a combination of biodegradable and non-biodegradable, depending on the desired duration of the reinforcement function of the prosthesis.

If a non permanent reinforcement is desired, the synthetic biocompatible material may be biodegradable. A suitable synthetic biocompatible material may be polylactic acid or copolymers thereof.

If a permanent reinforcement is desired the synthetic biocompatible material may be non biodegradable.

In embodiments, the synthetic biocompatible material is a synthetic non-biodegradable material. Embodiments where the synthetic biocompatible material is non-degradable allow a long term reinforcement of the tissue to be reinforced or repaired.

In embodiments, the biocompatible polymer material is selected from polypropylene, polyethylene terephthalate, and mixtures thereof.

In embodiments, the biocompatible polymer material is polypropylene.

In embodiments, the monofilament has a diameter of from about 0.08 mm to about 0.25 mm, preferably from about 0.10 mm to 0.15 mm, more preferably of about 0.11 mm, 0.12 mm, or 0.13 mm, more preferably 0.12 mm. Such a diameter allows obtaining a good size of the pores and providing the knit with a lightweight and flexible structure, while maintaining good mechanical properties. In embodiments, the monofilament has a diameter of about 0.12 mm.

The knit of the prosthesis of the invention is porous. Knits may comprise openings or pores which may be generated by the pattern followed for the knitting of yarns forming the knit.

In embodiments, the knit of the prosthesis of the invention comprises a plurality of pores having a diameter above 1 mm. In particular, the plurality of pores having a diameter above 1 mm defines an efficient porosity of said knit ranging from about 35% to about 70%, preferably of about 55%.

By "efficient porosity" is meant according to the present application a porosity taking into account only the pores having a diameter above 1 mm, while leaving out the pores having a diameter less or equal to 1 mm. By "pores having a diameter above 1 mm" is meant the pores which have dimensions greater than 1 mm in all directions. The efficient porosity therefore corresponds to the ratio of the area of the totality of the pores having a diameter above 1 mm as defined above to the area of the totality of the knit studied. The pores having a diameter above 1 mm are measured with a profile projector such as a projector 300V from ORAMA. The "efficient porosity" and its measuring method are described in the publication "*New objective measurements to characterize the porosity of textile implants*", T. Mühl, M. Binnebösel, U. Klinge and T. Goedderz, Journal of Biomedical Materials Research Part B: Applied Biomaterials, p. 176-183.

The efficient porosity as described above is useful for characterizing the ability of the knit of the prosthesis of the invention to favor cell colonization. Indeed, pores having a diameter above 1 mm are particularly desired for tissue ingrowth after implantation.

In embodiments, the knitting pattern of the knit of the prosthesis of the invention defines a plurality of pores having a diameter ranging above 1 mm. The pores may have a substantially hexagonal or circular shape.

In embodiments, the knit of the invention comprises a plurality of pores having a diameter above 2 mm. Such knits with pores having a diameter above 2 mm favor cell colonization and exhibit a good transparency allowing the surgeon to have a better visibility of the surrounding tissues when he puts the knit/prosthesis in place at the implantation site.

A suitable porous knit for the prosthesis of the invention is for example a knit based on a monofilament of polypropylene of diameter 0.12 mm, the pattern followed for the knitting of said monofilament on a knitting machine having two guide bars B1, B2 being the following, according to the ISO 11676 standard:

Bar B1: 1.2/4.5/4.3/4.5/4.3/1.0/1.2/1.0//
Bar B2: 4.3/1.0/1.2/1.0/1.2/4.5/4.3/4.5//

Guide bars B1 and B2 may be threaded 1 full 1 empty and may move symmetrically.

The knitting machine may be a warp knitting machine or a raschel knitting machine.

Another suitable knit for the prosthesis of the invention is obtained by knitting a monofilament of polypropylene of diameter 0.10 mm on a warp knitting machine having two guide bars B1, B2, according to the following pattern, according to the ISO 11676 standard:

Bar B1: 5.4/4.3/2.1/0.1/1.2/3.4//
Bar B2: 0.1/1.2/3.4/5.4/4.3/2.1//

Guide bars B1 and B2 are threaded 1 full 1 empty and move symmetrically.

The two above knitting patterns allow obtaining knits suitable for the present invention, having a plurality of pores having a diameter above 1 mm, an efficient porosity ranging from about 35% to about 70%, and a transparency allowing the surgeon to have a good visibility of the implantation site at the time he puts the knit or prosthesis in place.

The knit of the prosthesis of the invention is preferably lightweight. The knit of the prosthesis of the invention preferably shows a mass per unit area ranging from about 30 to about 70 g/m$^2$, preferably ranging from about 36 to about 50 g/m$^2$, and more preferably of about 44 g/m$^2$, 45 g/m$^2$, 46 g/m$^2$, 47 g/m$^2$ or 48 g/m$^2$, measured according to ISO 3801: 1977 «Determination of mass per unit length and mass per unit area», 5 specimens 1 dm$^2$. Such a low mass per unit area allows introducing only a little quantity of foreign material in the body of the patient.

In embodiments, the knit of the prosthesis of the invention has a tensile breaking strength in the warp direction of at least about 200 N, preferably of about 237 N. In embodiments, the knit of the prosthesis of the invention has a tensile breaking strength in the weft direction of at least about 170 N, preferably of about 201 N. In embodiments, the knit of the invention has a bursting strength of at least about 400 kPa, preferably of about 463 kPa. In embodiments, the knit of the prosthesis of the invention has a tear strength in the warp direction of at least about 25 N, preferably of about 30 N. In embodiments, the knit of the prosthesis of the invention has a tear strength in the weft direction of at least about 25 N, preferably of about 37 N. In embodiments, the knit of the prosthesis of the invention has a suture pull out strength in the warp direction of at least about 35 N, preferably of about 46 N. In embodiments, the knit of the prosthesis of the invention has a suture pull out strength in the weft direction of at least about 38 N, preferably of about 42 N. In embodiments, the knit of the prosthesis of the invention has a tensile strength of at least about 42 N/cm, preferably of about 47 N/cm.

The tensile breaking strength (N), the bursting strength (kPa), the tear strength (N), the suture pull out strength (N) and the tensile strength (N/cm) above are measured according to the methods as indicated in the below Examples of the present application.

The porous knit of the prosthesis of the invention shows preferably an homogeneous distribution of shear forces at fixation points. In particular, although it is provided with a lightweight structure, the porous knit of the prosthesis of the invention may show a good resistance to fracture at fixation points compared to lightweight knits of the prior art.

The prosthesis of the invention further comprises a synthetic non porous biodegradable film comprising at least a copolymer of at least ε-caprolactone. The film is intended to cover at least part of the first face of the knit. In embodiments, the synthetic non porous biodegradable film of the prosthesis of the invention entirely covers the first face of the porous knit, and more preferably projects beyond the edges of the knit in such a way as to protect the prosthesis from contacts with adjacent biological tissues, the overshoot being from 5 to 10 millimeters for example. The synthetic non porous biodegradable film of the prosthesis of the invention is intended to minimize post-surgical adhesions on the first face of the knit by occluding the pores present on the surface of said first face. The synthetic non porous biodegradable film of the prosthesis of the invention is preferably continuous and has a smooth and even surface.

In embodiments, the synthetic non porous biodegradable film is a film obtained by extrusion of a composition comprising at least a copolymer of at least ε-caprolactone. In embodiments, the synthetic non porous biodegradable film is a film obtained by extrusion of a composition comprising, preferably consisting in, a random copolymer of glycolide, ε-caprolactone, trimethylene carbonate and lactide.

In embodiments, the synthetic non porous biodegradable film is a film obtained by extrusion of a composition consisting in a random copolymer of from about 68.5 to about 71.5 mole percent glycolide, from about 14.7 to about 17.5 mole percent ε-caprolactone, from about 6.7 to about 8.6 mole percent trimethylene carbonate and from about 4.6 to about 6.5 mole percent lactide. The preparation of copolymer composition suitable for forming the film of the prosthesis of the invention is described in U.S. Pat. No. 6,235,869.

The film may be obtained by flat-die extrusion of the composition comprising at least a copolymer of at least ε-caprolactone in an extruder at a temperature ranging from 170° C. to 210° C. Further to extrusion, the film may be annealed according to conventional methods.

The film of the prosthesis of the invention is biodegradable. In embodiments, the film of the prosthesis of the invention preferably degrades in vivo in less than 15 weeks. A film with such degradation kinetics allows limiting the presence of foreign material within the body of the patient while being efficient with regard to prevention of post-surgical adhesions.

In embodiments, the synthetic non porous biodegradable film shows a thickness ranging from about 15 μm to about 25 μm. In embodiments, the thickness of the film is about 20 μm. In embodiments, the thickness of the film is about 25 μm. Films with such thicknesses constitute efficient adhesion barriers with limited risk of inflammatory response. In addition, films with such thicknesses allow the resulting prosthesis to remain globally thin and soft, and therefore particularly adapted to be folded for easy introduction in a trocar.

The prosthesis of the invention further comprises a synthetic biodegradable binder for bonding the film to the first face of the knit. The binder comprises at least a polymer of ε-caprolactone.

In embodiments, the binder consists in a polymer of ε-caprolactone, in particular in a polymer of ε-caprolactone having a molecular weight of about 80000 g/mol. Such a polymer of ε-caprolactone allows a good binding of the film to the first face of the knit even if the polymer of ε-caprolactone is present in a limited amount. Such a polymer of ε-caprolactone therefore allows obtaining an efficient binding of the film to the first face of the knit while limiting the amount of foreign materials introduced in the body of the patient.

In embodiments, in particular where the binder consists in a polymer of ε-caprolactone, for example in a polymer of ε-caprolactone having a molecular weight of about 80000 g/mol, the binder is present in the prosthesis, in particular between the film and the first face of the knit, in an amount ranging from about 0.60 mg/cm$^2$ to about 0.95 mg/cm$^2$, preferably ranging from about 0.70 mg/cm$^2$ to about 0.85 mg/cm$^2$, more preferably of about 0.83 mg/cm$^2$.

In embodiments, in particular where the binder consists in a polymer of ε-caprolactone, for example in a polymer of ε-caprolactone having a molecular weight of about 80000 g/mol, the binder is present in an amount ranging from 6% to 11% by weight, with respect to the weight of the prosthesis. The binder therefore represents a limited amount of the weight of the prosthesis and a limited amount of additional foreign material introduced in the body of the patient.

The binder is present between said film and said first face under the form of a discontinuous layer. By "discontinuous layer of material" is meant in the present application a plurality of discrete amounts of material which are not linked to each other and which do not form a continuous film. The binder of the prosthesis of the invention is present between said film and said first face under the form of a plurality of discrete amounts of binder which are not linked to each other and which do not form a continuous film. For example, the presence of the binder on the first face of the knit may be limited to the surface of the fibers of the monofilament forming the knit, preferably on the top surface of such fibers, with no binder present in the pores of the knit. In addition, preferably, no binder material is present on the surface of the second face of the knit. The binder therefore may not form a continuous layer between the first face of the knit and the film.

When the binder consists in a polymer of ε-caprolactone, the prosthesis comprises a limited number of different chemical materials, as ε-caprolactone is also a component of the film. This allows limiting the number of different foreign materials introduced in the body of the patient.

A polymer of ε-caprolactone having a molecular weight of about 80000 g/mol suitable for the binder of the prosthesis of the invention is the product commercially available under the code 440744 from company Sigma-Aldrich.

The non porous film of the prosthesis of the invention is intimately linked to the first face of the knit by the binder, although the amount of binder per surface area on the first face of the knit is limited and although the binder may be present under the form of a discontinuous layer.

The prosthesis of the invention may be further provided with one or more marking(s) bearing information that may be useful to the surgeon, in particular at the time of selecting the prosthesis and/or at the time of positioning the prosthesis inside the body of the patient. For example, the marking may indicate the size of the prosthesis, the direction of the longitudinal axis or transversal axis in case the prosthesis is rectangular, the center of the prosthesis, etc. . . . The marking may also indicate to the surgeon the face of the prosthesis which is open to cell colonization or, on the contrary, the face that is covered by the film for minimizing post-surgical adhesions.

In embodiments, the prosthesis is provided with at least a marking made of a synthetic biodegradable material. In embodiments, the marking is located between the binder and the film. In other embodiments, the marking is located between the first face of the knit and the binder. The marking may be present under the form of one piece of marking or several pieces of markings, like letters, digits, spots, dots, geometric figures and the like. In the present application the expression "marked zone" will refer to a zone of the prosthesis, in particular of the first face of the knit, where at least a piece of marking is present.

In embodiments, the total surface area of the marked zones of the prosthesis on a face of the prosthesis may represent from about 0.8% to about 4% of the total surface area of said face of the prosthesis.

In embodiments, the marking is made from a composition consisting in a dye solubilized in a solution of a polymer of ε-caprolactone. In other embodiments, the marking is made from a composition consisting in a dye solubilized in a solution of a copolymer of lactic acid and glycolic acid.

In embodiments, the synthetic biodegradable material forming the marking consists in a polymer of ε-caprolactone and a dye, for example D&C Violet N° 2. In embodiments, the weight ratio of the dye, for example D&C Violet N° 2, to the polymer of ε-caprolactone is equal or less than 1/1000.

In embodiments where the synthetic biodegradable material forming the marking consists in a polymer of ε-caprolactone and a dye, in particular D&C Violet N° 2, the synthetic biodegradable material forming the marking is present, in particular between the first face of the knit and the binder, in an amount ranging from about 3.2 mg/cm$^2$ to about 4.0 mg/cm$^2$, in the marked zones of the prosthesis.

When the synthetic biodegradable material forming the marking consists in a polymer of ε-caprolactone and D&C Violet N° 2, and when the binder consists in a polymer of ε-caprolactone, the amount of polymer of ε-caprolactone and D&C Violet N° 2 in the marked zones of the prosthesis may range from 3.7 mg/cm² to about 4.6 mg/cm². In such embodiments, the amount of polymer of ε-caprolactone in the marked zones of the prosthesis remains limited.

When the synthetic biodegradable material forming the marking consists in polymer of ε-caprolactone and a dye, the prosthesis comprises a limited number of different chemical materials, as ε-caprolactone is also a component of the film and of the binder. This allows limiting the number of different foreign materials introduced in the body of the patient.

In addition, when the synthetic biodegradable material forming the marking consists in a polymer of ε-caprolactone and a dye, the degradation kinetics of the synthetic biodegradable material forming the marking is very close to that of the binder. The degradation process of the synthetic biodegradable material forming the marking and of the binder are therefore similar and do not affect each other.

Another aspect of the invention is a method for forming the prosthesis above comprising the following steps:
  a) providing a porous knit made from a monofilament of a synthetic biocompatible material, said knit defining two opposite faces, a first face and a second face,
  b) providing a synthetic non porous biodegradable film comprising at least a copolymer of at least ε-caprolactone,
  c) gluing the first face of the knit with a binding solution comprising at least a polymer of ε-caprolactone, so as to form a discontinuous layer of binding solution on the first face of the knit,
  d) laminating the film of step b) on the glued first face of the knit.

In a first step of the method of the invention, step a), a porous knit made from a monofilament of a synthetic biocompatible material is provided. Suitable porous knits for the prosthesis of the invention and the method for manufacturing them is described above in the present application.

Following knitting, the knit may be heat-set, for example on a heat-setting machine according to conventional methods.

In a second step of the method of the invention, step b), a synthetic non porous biodegradable film comprising at least a copolymer of at least ε-caprolactone is provided. Suitable films for the prosthesis of the invention and their manufacture method are described above.

In a third step of the method of the invention, step c), the first face of the knit obtained in step a) is glued with a binding solution so as to form a discontinuous layer of binding solution on the first face of the knit.

In embodiments, a composition of a polymer of ε-caprolactone in a solvent such as methylene chloride is used for binding the film to the first face of the knit. For example, the composition is sprayed on the first face of the knit in order to glue said first face of the knit.

In embodiments, the binding solution is a solution of 3% (w/v) of a polymer of ε-caprolactone in methylene chloride. For example, a solution comprising a polymer of ε-caprolactone in an amount of 30 g/L in methylene chloride is used for binding the film to the first face of the knit.

In embodiments, the spraying is performed with a spraying machine «SONOTEK Flexicoat» with a microflow pump. In embodiments, the spraying step may comprise several repeated passes of the spraying nozzle on the first face of the knit.

In embodiments, the binding solution, in particular a solution of 3% (w/v) of a polymer of ε-caprolactone in methylene chloride, is sprayed on the surface of the first face of the knit. In embodiments, the binding solution, in particular a solution of 3% (w/v) of a polymer of ε-caprolactone in methylene chloride, is sprayed on the surface of the first face of the knit so as to form a discontinuous layer of binding solution. In embodiments, the binding solution, in particular a solution of 3% (w/v) of a polymer of ε-caprolactone in methylene chloride, is sprayed on the surface of the first face of the knit at a delivery rate of the solution of about 10 mL/min. The spraying may be repeated several times. For example, the binding solution, in particular a solution of 3% (w/v) of a polymer of ε-caprolactone in methylene chloride, is sprayed on the surface of the first face of the knit via 3 passes of a spraying nozzle, with a delivery rate of the solution of about 10 mL/min for each pass.

In embodiments, during the spraying and subsequent natural drying, the solvent, in particular the methylene chloride, evaporates totally. The binder left on the first face of the knit therefore consists in the polymer of ε-caprolactone.

The spraying conditions of the binding solution, in particular a delivery rate of the solution of about 10 mL/min, allows the binding solution, and in the end the remaining binder after complete evaporation of the solvent such as methylene chloride, to be distributed on the surface of the first face of the knit under the form of a discontinuous layer, and in particular on top of the monofilament fibers of the surface of the first face of the knit, with no binding solution/binder present in the pores present at the surface of said first face of the knit, and with no binding solution/binder present on the surface of the second face of the knit.

In addition, such spraying conditions, for example a delivery rate of the solution of about 10 mL/min and a number of 3 passes, allow obtaining a limited amount of binder in the final product, namely the prosthesis, such as an amount ranging from about 0.60 mg/cm² to about 0.95 mg/cm², preferably ranging from about 0.70 mg/cm² to about 0.85 mg/cm², more preferably of about 0.83 mg/cm² between the film and the first face of the knit.

In a fourth step of the method of the invention, step d), the film of step b) is laminated on the glued face of the knit.

The lamination may be performed on a press machine comprising a bottom plate and a top heating plate.

In embodiments, the lamination step is performed by contacting the film of step b) with the glued face of the knit obtained at step c) during a time period ranging from about 30 s to about 7 min, preferably of about 5 minutes, at a temperature of about 105° C. with a contact pressure ranging from about 137895 Pa (20 psi) to about 1034213 Pa (150 psi), preferably of about 172369 Pa (25 psi).

For example, the knit may be positioned on the bottom plate of the machine, with the glued face of the knit in the upward direction. The film obtained at steb b) may then be positioned on the glued face of the knit. The temperature of the top heating plate may be set at about 105° C. The heating plate may be left in contact with the knit and film at the desired contact pressure, for example about 172369 Pa (25 psi), during the desired time period, for example a time period of about 5 minutes.

The method of the invention allows obtaining an efficient bonding of the film to the knit without having to glue the film itself. An additional step of gluing the film is therefore avoided with the method of the invention. The method is therefore simplified with respect to existing methods in which the film needs to be also glued.

In particular, the gluing step conditions and the lamination step conditions of the method of the invention combined with the use of a solution of 3% (w/v) of a polymer of ε-caprolactone in methylene chloride as the binding solution allow obtaining an intimate binding between the film and the first face of the knit, although the amount of binder per surface area between the film and the first face of the knit in the resulting prosthesis may be limited and although the binder in the resulting prosthesis may be present under the form of a discontinuous layer between the film and said first face.

The resulting prosthesis of the invention allows performing an efficient reinforcement of tissue while minimizing post surgical adhesions with reduced number and amount of foreign materials of different compositions that are implanted in the body of the patient.

Before gluing the first face of the knit in view of laminating the film, a printing step may be performed in order to provide the first face of the knit with one or more marking (s).

In embodiments, the printing step comprises positioning a mask on the first face of the knit and spraying a dying solution on the first face of the knit provided with said mask. The mask generally is designed so as to allow one or more part(s) of the first face of the knit to receive the dying composition and therefore be printed while protecting the rest of the surface of said first face. The mask therefore may be designed so as to allow the printing of any desired geometric figures, such as letters, figures, etc. . . . on the first face of the knit.

In embodiments, a composition of a polymer of ε-caprolactone in a solvent such as methylene chloride is used for solubilizing a dye intended to be used as a marking for the prosthesis of the invention. The composition may be sprayed on the first face of the knit provided with a mask. One or more marking(s) are therefore obtained.

In embodiments, a solution comprising a polymer of ε-caprolactone in an amount of 30 g/L in methylene chloride is used for solubilizing 0.03 g/L of dye. In embodiments, the dye is D&C Violet N° 2. In embodiments, a solution comprising a polymer of ε-caprolactone in an amount of 30 g/L in methylene chloride is used for solubilizing 0.03 g/L of D&C Violet N° 2. Such a solution corresponds to a solution of 3% (w/v) of a polymer of ε-caprolactone in methylene chloride and 0.1% (w/w) of D&C Violet N° 2 in a polymer of ε-caprolactone.

In embodiments, the dying solution is a solution of 3% (w/v) of a polymer of ε-caprolactone in methylene chloride and 0.1% (w/w) of D&C Violet N° 2 in a polymer of ε-caprolactone.

In embodiments, the spraying is performed with a spraying machine «SONOTEK Flexicoat» with a microflow pump. In embodiments, the spraying step may comprise repeated passes of the spraying nozzle on the first face of the knit provided with the mask.

In embodiments, the dying solution, in particular a solution of 3% (w/v) of a polymer of ε-caprolactone in methylene chloride and 0.1% (w/w) of D&C Violet N° 2 in a polymer of ε-caprolactone, is sprayed on the surface of the first face of the knit provided with the mask. In embodiments, the dying solution, in particular a solution of 3% (w/v) of a polymer of ε-caprolactone in methylene chloride and 0.1% (w/w) of D&C Violet N° 2 in a polymer of ε-caprolactone, is sprayed on the surface of the first face of the knit provided with the mask with a delivery rate of the solution of about 10 mL/min.

The spraying may be repeated several times depending on the color intensity that is desired for the marking. In embodiments, the dying solution, in particular a solution of 3% (w/v) of a polymer of ε-caprolactone in methylene chloride and 0.1% (w/w) of D&C Violet N° 2 in a polymer of ε-caprolactone, is sprayed via 13 passes of a spraying nozzle on the surface of the first face of the knit provided with the mask, with a delivery rate of the solution of about 10 mL/min.

In embodiments, during the spraying and subsequent natural drying, the solvent, in particular the methylene chloride, evaporates totally. The marking left on the first face of the knit once the mask is removed therefore consists in the polymer of ε-caprolactone and the D&C Violet N° 2.

Such an amount of dying composition and conditions for the printing step allow having simultaneously an efficient marking regarding colorimetric intensity, so that the marking may be easily seen by the surgeons, and a limited amount of foreign materials within the patient body.

In addition, such spraying conditions allow obtaining a limited amount of marking material in the final product, namely the prosthesis, such as an amount ranging from about about 3.2 mg/cm$^2$ to about 4.0 mg/cm$^2$ in the marked zones of the knit.

The prosthesis of the invention may be packaged and sterilized using conventionally known techniques.

The prosthesis of the invention allows performing an efficient reinforcement of tissue while minimizing post surgical adhesions with reduced number and amount of foreign materials of different compositions that are implanted in the body of the patient. The prosthesis of the invention is also particularly efficient regarding cell colonization. The efficient porosity of the porous knit allows an optimal tissue integration on the second face of the knit.

Moreover, the prosthesis of the invention is soft and easily foldable. The prosthesis of the invention may therefore be easily introduced into a trocar and is particularly adapted in laparoscopy surgery.

The prosthesis of the invention can be implanted in intraperitoneal site for ventral hernia repair via open or laparoscopic approach. Fixation to the surrounding tissues can be achieved by stapling, conventional sutures or other means.

Another aspect of the invention is a hernia prosthesis comprising a knit as described above.

BRIEF DESCRIPTION OF DRAWINGS

The present invention will become clearer from the following Examples and drawing in which.

DETAILED DESCRIPTION OF EMBODIMENTS

Examples

In all the below examples, the polymer of ε-caprolactone used is a polymer of ε-caprolactone having a molecular weight of about 80000 g/mol commercially available under the product code 440744 from company Sigma-Aldrich.

Example 1

The present example describes the manufacture of knits suitable for the prosthesis of the invention.

1°) Manufacture of Porous Knit A:

Knit A is produced by knitting on a warp knitting machine or a raschel knitting machine having two guide bars B1, B2, a monofilament of polypropylene of diameter 0.12 mm, the pattern followed for the knitting of the monofilament being the following, according to the ISO 11676 standard:
Bar B1: 1.2/4.5/4.3/4.5/4.3/1.0/1.2/1.0//
Bar B2: 4.3/1.0/1.2/1.0/1.2/4.5/4.3/4.5//
Guide bars B1 and B2 are threaded 1 full 1 empty and move symmetrically.

The knitting pattern of Knit A produces pores greater than about 1.0 mm in diameter. For example, some pores of Knit A have an average size of 2.0×2.4 mm. Such a large size of pores is very favorable for cell colonization and confers to Knit A a good transparency allowing a good visibility at the implantation site.)

2°) Manufacture of Porous Knit B:

Knit B is obtained by knitting a monofilament of polypropylene of diameter 0.10 mm on a warp knitting machine having two guide bars B1, B2, according to the following pattern, according to the ISO 11676 standard:
Bar B1: 5.4/4.3/2.1/0.1/1.2/3.4//
Bar B2: 0.1/1.2/3.4/5.4/4.3/2.1//
Guide bars B1 and B2 are threaded 1 full 1 empty and move symmetrically.

After knitting, the knits A and B are heat-set according to conventional methods.)

3°) Properties of Knits A and B:

The following properties of knits A and B have been determined as follows:

Mass per unit area (g/m$^2$): measured according to ISO 3801: 1977 «Determination of mass per unit length and mass per unit area», 5 specimens 1 dm$^2$, pore size (width×height) (mm): knit biggest pores are measured making one measurement on 10 individual samples with a profile projector such as a projector 300V from ORAMA, Bursting strength (kPa): measured according to ISO 13938-2: 1999 "Textiles—Bursting properties of textiles—Pneumatic method for determining the bursting strength and bursting deformation", 5 samples Tensile strength (N/cm) is measured through a plunger test with a traction testing machine such as the Hounsfield model H5KS (Hounsfield, Redhill, England)., crosshead speed: 50 mm/min, 5 samples: the burst pressure can be determined using a circular mesh sample with a radius of $R_m$=56.4 mm and with a test area of 100 cm$^2$ clamped at the outward boarder (modified DIN 54307 superseded standard). Then, the mesh is loaded with a spherical stamp of a radius $R_s$=50 mm, velocity v=50 mm/min until rupture occurs. Based on the measured forces and the resulting stretch, the tensile strength (N/cm) can be calculated;

Tear strength (N) in the warp direction and in the weft direction: measured according to ISO 4674:1977 "Textiles covered with rubber or plastic—Determination of the tear strength" Method A2, 5 samples, width: 75 mm, Tear length≤145 mm, crosshead speed: 100 mm/min, Thickness: is measured according to ISO 9073-2: 1997 "Textiles—test methods for nonwovens—Part 2: Determination of thickness", 10 samples, 100×50 mm, Tensile breaking strength and elongation at break: is measured according to ISO 13934-1: 2013 "Textiles—Tensile properties of fabrics—Part 1: Determination of maximum force and elongation at maximum force using the strip method", 5 samples, width: 50 mm, Length: 200 mm between the jaws, Crosshead speed: 100 mm/min, Pre-load: 0.5 N, using a traction testing machine such as the Hounsfield model HSKS (Hounsfield, Redhill, England);

Effective porosity: pores having a diameter above 1 mm are measured with a profile projector such as a projector 300V from ORAMA, 1 sample of 100×50 mm;

Suture pull out strength in the warp direction and in the weft direction measured according to NF S94-801: 2007 "Reinforcement implants introduced by the vaginal route for the treatment of stress urinary incontinence and/or of prolapse of the pelvic organs—preclinical trials and clinical trials"-§ 5.3.3 5 specimens 50×100 mm, USP 2 suture yarn, crosshead speed: 100 mm/min, using a traction testing machine such as the Hounsfield model H5KS (Hounsfield, Redhill, England).

The results are collected in the following tables:

TABLE I mechanical properties

|  | Knit A | | Knit B | |
| --- | --- | --- | --- | --- |
|  | Warp | Warp | Weft | Weft |
| Tensile breaking strength (N) | 237 ± 6 | 187 ± 16 | 149 ± 10 | 201 ± 6 |
| Elongation under 50N (%) | 38 ± 1 | 43 ± 1 | 59 ± 1 | 46 ± 0 |
| Bursting strength (kPa) | 463 ± 19 | | 361 ± 38 | |
| Tear strength (N) | 30 ± 1 | 23 ± 2 | 22 ± 3 | 37 ± 5 |
| Suture pull out strength (N) | 46 ± 5 | 33 ± 1 | 33 ± 2 | 42 ± 3 |
| Tensile strength (N/cm) | 47 ± 1 | | 40 ± 1 | |

TABLE II mass per unit area and porosity

|  | Knit A | Knit B |
| --- | --- | --- |
| Mass per unit area (g/cm$^2$) | 46 | 36 |
| Thickness (mm) | 0.6 | 0.4 |
| Pore size (mm) (width × height) | 2.0 × 2.4 | 1.6 × 1.4 |
| Efficient porosity (%) | 55 | 35 |

Example 2

The present example describes the preparation of a marked knit suitable for the prosthesis of the invention.

Knit A of Example 1 is provided with markings in accordance with the following method:

a) Preparation of the Dying Solution:

A mother solution of 0.1% (w/v) of dye in methylene chloride is first prepared as follows: 200 mg of D&C Violet N° 2 are added to 200 mL of methylene chloride with mixing.

The dying solution, under the form of a solution of 3% (w/v) of a polymer of ε-caprolactone in methylene chloride and 0.1% (w/w) of D&C Violet N° 2 in a polymer of ε-caprolactone is then prepared as follows:

18 mL of the mother solution of 0.1% (w/v) of dye in methylene chloride is added to 582 mL of methylene chloride. 18 g of polymer ε-caprolactone are added to the solution with mixing. The mixing is continued until total solubilization of the polymer of ε-caprolactone.

b) Spraying of the Dying Solution:

A mask provided with void zones and filled zones is positioned on a first face of Knit A, namely on the face of Knit A on which it is intended to apply the adhesion barrier film in a subsequent step. The filled zones of the mask are intended to protect the zones of the first face of Knit A that are not intended to be marked. The filled zones of the mask will therefore prevent these zones of the first face of Knit A to be contacted by the dying solution and to be printed. The void zones of the mask are intended to allow the dying solution to reach the zones of the first face of Knit A that are intended to be marked. To the void zones of the mask will correspond the marked zones of the first face of Knit A.

The dying solution prepared in a) above is then sprayed on the first face of Knit A provided with the mask according to the following method: the spraying is performed with an ultrasonic spraying machine «SONOTEK Flexicoat» with a Sonotek 48 KHz Impact Nozzle and a microflow pump with the following conditions:

Nozzle speed: 100 mm/s
Height of the nozzle with respect to the knit: 40 mm
Space between two nozzle passages: 8 mm
delivery rate of the solution: 10 mL/min The spraying is performed under the form of 13 passes of the spraying nozzle. During the spraying, the methylene chloride totally evaporates.

At the end of the 13 passes of the spraying nozzle, and after evaporation of the methylene chloride, the synthetic biodegradable material forming the marking, namely the polymer ε-caprolactone and D&C Violet N° 2, is present on the first face of Knit A in an amount of about 3.50 mg/cm$^2$ in the marked zones of the first face of Knit A.

Such an amount of marking material allows having simultaneously an efficient marking regarding colorimetric intensity, so that the marking may be easily seen by the surgeons, and a limited amount of foreign materials within the patient body.

Example 3

The present example describes the manufacture of a sample of a prosthesis of the invention according to the method of the invention.)

1°) Gluing of Knit A:

The first face of Knit A with marked zones as obtained at EXAMPLE 2 above is glued with a binding solution in accordance with the following method:

A solution of 3% (w/v) of a polymer of ε-caprolactone in methylene chloride is prepared as the binding solution.

The binding solution is then sprayed on the first face of Knit A provided with marked zones according to the following method: the spraying is performed with an ultrasonic spraying machine «SONOTEK Flexicoat» with a Sonotek 48 KHz Impact Nozzle and a microflow pump with the following conditions:

Nozzle speed: 100 mm/s
Height of the nozzle with respect to the knit: 40 mm
Space between two nozzle passages: 8 mm
delivery rate of the solution: 10 mL/min The spraying is performed under the form of 3 passes of the spraying nozzle. During the spraying, the methylene chloride totally evaporates.

Such spraying conditions of the binding solution, in particular a delivery rate of the solution of 10 mL/min, allow the binding solution, and in the end the binder after complete evaporation of the methylene chloride, to be distributed under the form of a discontinuous layer on the surface of the first face of the knit. Indeed, these spraying conditions allow only a limited amount of binding solution to be spread on the first face of Knit A at each pass of the nozzle. The binding solution is therefore not drawn downwards by gravity at each pass and remains significantly on the top surface of the fibers of the face of the knit on which it is sprayed. Thanks to these spraying conditions, the binding solution does not migrate towards the opposite face (second face) of the knit. The binder therefore remains present at the surface of the first face of Knit A and is available for completing an efficient bonding of the film to the first face of the knit once the lamination step is completed (see below).

For example, with spraying conditions where the solution rate is 20 mL/min at each pass of the nozzle, the binding solution is more prone to migrate towards the opposite face of the knit. Less binder is available in the end for performing the bonding between the first face of the knit and the film during the lamination step to come.

At the end of the 3 passes of the spraying nozzle at a delivery rate of the solution of 10 mL/min, and after evaporation of the methylene chloride, the binder, namely the polymer of ε-caprolactone, is present on the first face of Knit A in an amount of about 0.83 mg/cm$^2$ in the non marked zones of the first face of Knit A.

At the end of the 3 passes of the spraying nozzle at a delivery rate of the solution of 10 mL/min, and after evaporation of the methylene chloride, the binder and the marking material, namely the polymer of of ε-caprolactone and D&C Violet N° 2, are present on the first face of Knit A in an amount of about 4.33 mg/cm$^2$ in the marked zones of the first face of Knit A.

As will appear from the description below, such an amount of the binding solution allows obtaining an efficient binding of the film to the knit while limiting the amount of foreign materials in the body of the patient.)

2) Lamination of the Non Porous Film on the Glued Face of Knit A:

A rectangular shaped sample of the marked Knit A above of dimensions 10.5 cm×20.5 cm is prepared.

A non porous biodegradable film comprising at least a copolymer of at least ε-caprolactone under the form of an extruded film obtained by flat-die extrusion of a composition consisting in a random copolymer of from about 68.5 to about 71.5 mole percent glycolide, from about 14.7 to about 17.5 mole percent ε-caprolactone, from about 6.7 to about 8.6 mole percent trimethylene carbonate and from about 4.6 to about 6.5 mole percent lactide, is provided. This film has a thickness of about 20 µm.

A rectangular shaped sample of the film above of dimensions 11 cm×22 cm is prepared.

The lamination is performed with a press from Nelipak comprising a bottom plate and a top heating plate.

The sample of Knit A is positioned on the bottom plate of the machine, with its glued face up.

The sample film is positioned on top of Knit A, so that the surface area on which the pressure is intended to be applied is 20.5 cm×8.5 cm.

A flap of about 3 cm of Knit A and of film is left out of the machine. This flap will not be laminated and will enable performing peel tests on the laminated sample.

The starting pressure of the machine is set up at $1.5 \ 10^5$ Pa (1.5 bar). The temperature of the top heating plate is set at about 105° C. The top heating plate is moved and put in contact with the film so as to press it against the glued face of the knit, and the efficient pressure exerted on the sample is about 172369 Pa (25 psi). The contact time is of 5 minutes.

A synthetic prosthesis of the invention is obtained. The film is intimately linked to the first face of Knit A by the binder, and cannot be delaminated, while at the same time maintaining the porosity open on the second surface of the knit. In particular, the film is intimately linked to the first face of Knit A by the binder, although the amount of binder per surface area on the first face of Knit A is limited.

In the present example, the binder is present in an amount of about 9% by weight, with respect to the weight of the prosthesis.

Figure 1:
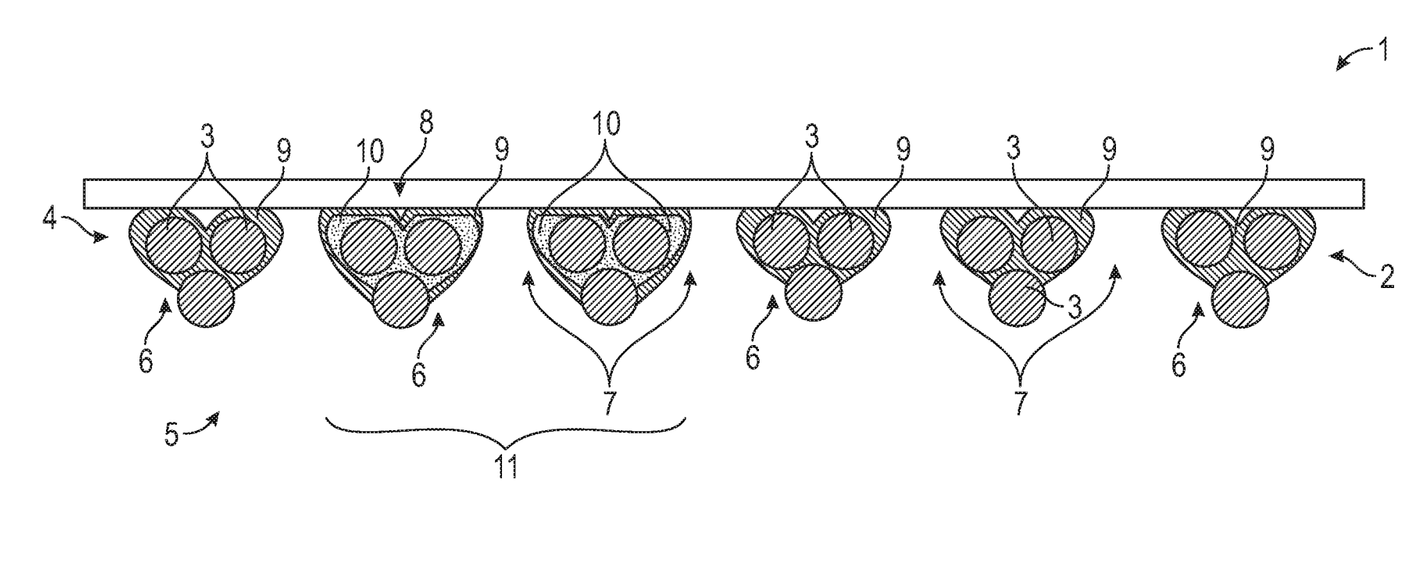
FIG. 1 is a cross section view of an embodiment of a prosthesis of the invention.

Wth reference to FIG. 1 is shown a cross section view of the prosthesis 1 of the invention of the present Example obtained by the method of the present Example.

The prosthesis 1 comprises a porous knit 2 (Knit A) made from monofilaments 3 of polypropylene as described above. The knit 2 defines two opposite faces, a first face 4 and a second face 5. The cross section of the knit 2 shown on FIG. 1 shows an alternance of stitches 6, each stitch 6 involving three monofilaments 3, and pores 7.

The prosthesis 1 further comprises a non porous biodegradable film 8, the film as described above, covering the first face 4 of the knit 2. The second face 5 of the knit is left open for cell colonization.

The film 8 is bonded to the first face 4 of the knit 2 by means of the binder 9. As appears on this figure, the binder 9 is under the form of a discontinuous layer of material. In particular, as explained above, the binder 9 is present under the form of a plurality of discrete amounts of binder material which are not linked to each other and which do not form a continuous film. No binder is present in the pores 7 of the knit 2 and no binder is present on the surface of the second face 5 of the knit 2.

The discrete structure of the binder 9 between the first face 4 of the knit 2 and the film 8 allows an improved global tissue integration of the prosthesis 1 after implantation. Indeed, the discontinuous structure of the binder 9 allows the cell colonization to further develop on the first face 4 of the knit 2 when the film 8 begins biodegrade after a few weeks, at a time when post-surgical adhesions are no more likely to occur and the film 8 has completed its function of prevention of adhesions. The cell colonization via the first face of the knit 2, after the non porous film 8 has begun its biodegradation, is therefore not impeded or delayed by the presence of the binder 9.

On FIG. 1 is further shown the marking 10 which is present in a marked zone 11 of the knit 2.)

3°) Peeling Strength:

A peeling test was performed in order to check the peeling strength of the film and to check the efficiency of the bonding between the film and the first face of Knit A. The idea is to measure the energy necessary to peel the film. The higher the necessary energy, the more efficient the bonding between the film and the knit.

The peeling strength measuring method is the following: a traction machine with a bottom fixed jaw and a top mobile jaw is used. The load cell is of 50 N. The distance between the two jaws before the test begins is 3 cm.

A rectangular shaped sample of the knit above is prepared by cutting a strip of 2.54 cm width and 8.5 cm length in the knit above, with maintaining the 3 cm long flap. The free end of the knit of the 3 cm flap described above is grasped within the bottom jaw. The free end of the film of the 3 cm flap described above is grasped within the top jaw. The sample to be tested is placed towards the user of the machine. Before any testing, the jaws are blocked at a pressure of 4 bars to ensure safe grasping of the sample.

The test is performed with the following parameters:
Temperature: 20° C.±2° C.,
Relative humidity: 65%±4%,
Test speed: 250 mm/min,
Preload: 0.25 N
Preload rate: 50 mm/min During the testing, the mobile jaw moves away from the fixed jaw. The energy (mJ) necessary for separating the film from the knit with a displacement between 60 mm and 150 mm is measured. The maximum force (N) necessary for delaminating the sample is also measured.

The energy and the maximum force are measured as described above for 15 samples manufactured as described in the present example. The results are the following:
average energy for the 15 samples: 429±37 mJ,
average maximum force for the 15 samples: 6.4±0.6 N These results confirm that the bonding of the film to the first face of Knit A is efficient. The film of the prosthesis of the invention is therefore very resistant to delamination.

Example 4

Two prostheses, prosthesis P1 and prosthesis P2, were manufactured, both with the Knit A of Example 1 above, the binding solution of Example 3 above and the non porous film of Example 3 above.

For prosthesis P1, the gluing step was completed so as to form a discontinuous layer of the binding solution on the first face of the knit A.

For prosthesis P2, the gluing step was completed by spraying the binding solution both on the first face of the knit A and on the face of the non porous film, so that the binding solution was present between the first face of the knit and the film under the form of a continuous layer of material.

Prostheses P1 and P2 were then submitted to the lamination step.

The structure of the final products were as follows:
in prosthesis P1: the binder was present between the non porous film and the first face of knit A under the form of a discontinuous layer,
in prosthesis P2: the binder was present between the non porous film and the first face of knit A under the form of a continuous layer.

Prostheses P1 and P2 were further surgically implanted in direct contact with subcutaneaous tissue in rats for 4 weeks (9 sites per prosthesis).

Tissue integration of the prostheses was evaluated as follows: a tissue ingrowth score representing a composite score involving consideration of the degree and nature of ongoing inflammation, fibroplasias, fibrosis, angiogenesis, and encapsulation was defined. This parameter and tissue integration has a maximum score of 4 (1=adequate, 2=good, 3=very good, 4=excellent).

Results for P1: overall tissue ingrowth and integration of the implanted prosthesis was very good to excellent (scores ranging from 3 to 4).

Resultas for P2: overall tissue ingrowth and integration of the implanted prosthesis was good to excellent (scores ranging from 2 to 4)

The method of the invention allows obtaining an efficient bonding of film to the first face of the knit while minimizing the presence of foreign materials implanted into the body of the patient.

The resulting prosthesis of the invention allows performing an efficient reinforcement of tissue while minimizing post surgical adhesions with reduced number and amount of foreign materials of different compositions that are implanted in the body of the patient.

The prosthesis of the invention is also particularly efficient regarding cell colonization. The efficient porosity of the knit, in particular of Knit A, allows an optimal tissue integration on the second face of the knit.

Moreover, the prosthesis of the invention is soft and easily foldable. The prosthesis of the invention may therefore be easily introduced into a trocar and is particularly adapted in laparoscopy surgery.

The invention claimed is:

1. A prosthesis for tissue reinforcement comprising:
 a lightweight porous knit defining a first face and a second face opposite the first face, the lightweight porous knit having a mass per unit ranging from about 36 to about 50 g/m$^2$ and an efficient porosity ranging from about 35% to about 70%,
 a synthetic non porous biodegradable film comprising at least a copolymer of at least ε-caprolactone, said film covering at least part of said first face,
 a synthetic biodegradable binder bonding said film to said first face, said binder comprising at least a polymer of ε-caprolactone, wherein said second face of said lightweight porous knit is left open to cell colonization.

2. A method for forming a prosthesis, comprising the following steps:
 a) providing a porous knit made from a monofilament of a synthetic biocompatible material, said knit defining two opposite faces, a first face and a second face,
 b) providing a synthetic non porous biodegradable film comprising at least a copolymer of at least ε-caprolactone,
 c) gluing the first face of the knit with a binding solution comprising at least a polymer of ε-caprolactone,
 d) laminating the film of step b) on the glued first face of the knit.

3. The method according to claim 2, wherein the binding solution is a solution of 3% (w/v) of a polymer of ε-caprolactone in methylene chloride.

4. The method according to claim 2, wherein the binding solution is sprayed on a surface of the first face of the knit at a delivery rate of the solution of about 10 mL/min.

5. The method according to claim 2, wherein the binding solution forms a discontinuous layer between the first face of the porous knit and the film.

6. The method according to claim 2, wherein the laminating step d) is performed by contacting the film of step b) with the glued face of the knit obtained at step c) during a time period ranging from about 30 s to about 7 min, at a temperature of about 105° C., with a contact pressure ranging from about 137,895 Pa to about 1,034,213 Pa (150 psi).

7. The method according to claim 6, wherein the contact pressure ranges from about 137,895 Pa to about 172,369 Pa.

8. The method according to claim 2, further comprising a step of printing one or more marking(s) on the first face of the knit, said printing being performed before step c).

9. The method according to claim 8, wherein the step of printing comprises positioning a mask on the first face of the knit and spraying a dying solution on the first face of the knit provided with said mask.

10. The method according to claim 9, wherein the dying solution is a solution of 3% (w/v) of a polymer of ε-caprolactone in methylene chloride and 0.1% of D&C Violet No 2 in a polymer of ε-caprolactone.

11. The method according to claim 10, wherein the dying solution is sprayed on the surface of the first face of the knit provided with the mask with a delivery rate of the solution of about 10 mL/min.

12. The method according to claim 2, wherein providing the porous knit includes knitting the monofilament on a knitting machine.

13. The method according to claim 12, wherein the knitting machine includes two guide-bars B1, B2 following a knit pattern, according to the ISO 11676 standard, including Bar B1: 1.2/4.5/4.3/4.5/4.3/1.0/1.2/1.0//

Bar B2: 4.3/1.0/1.2/1.0/1.2/4.5/4.3/4.5// or

Bar B1: 5.4/4.3/2, 1/0, 1/1.2/3.4//

Bar B2: 0.1/1.2/3.4/5.4/4.3/2.1//.

14. The method according to claim 13, wherein the guide-bars B1, B2 are threaded 1 full, 1 empty and move symmetrically.

15. The method according to claim 12, further comprising heat-setting the porous knit following knitting.

* * * * *